United States Patent [19]

Buysch et al.

[11] 4,252,750

[45] Feb. 24, 1981

[54] CYCLIC PHOSPHOROUS ACID ESTERS

[75] Inventors: Hans-Josef Buysch; Bert Brassat; Erich Eimers; Karl H. Hermann, all of Krefeld, Fed. Rep. of Germany

[73] Assignee: Bayer Aktiengesellschaft, Leverkusen, Fed. Rep. of Germany

[21] Appl. No.: 68,210

[22] Filed: Aug. 20, 1979

[30] Foreign Application Priority Data

Aug. 24, 1978 [DE] Fed. Rep. of Germany ....... 2837027

[51] Int. Cl.³ .......................... C07F 9/15; C08K 5/52
[52] U.S. Cl. ............................... 260/927 R; 260/936; 260/45.8 R; 260/37 N
[58] Field of Search ........................... 260/936, 927 R

[56] References Cited

U.S. PATENT DOCUMENTS

| 3,662,032 | 5/1972 | Kauder et al. | 260/936 |
| 3,907,939 | 9/1975 | Robin et al. | 260/936 |

FOREIGN PATENT DOCUMENTS

| 46-17896 | 5/1971 | Japan | 260/936 |
| 582257 | 11/1977 | U.S.S.R. | 260/936 |

*Primary Examiner*—Anton H. Sutto
*Attorney, Agent, or Firm*—Connolly and Hutz

[57] ABSTRACT

Phosphorous acid esters obtained by reacting bisphenols with phosphorous trihalogenide or triphosphite and optionally or mono - or polyhydroxy compound are especially useful for stabilizing polyamides.

2 Claims, No Drawings

CYCLIC PHOSPHOROUS ACID ESTERS

The present invention relates to novel phosphorous-acid esters and to their use as stabilisers for polyamides and to the thus stabilised polyamides.

It is known that polyamides can be stabilised against thermal and oxidative degradation by the addition of copper compounds in combination with halogen compounds. Although stabilisation in this manner is very effective, it is nevertheless attended by serious disadvantages, for example, important electrical properties of polyamides, such as surface resistance, volume resistivity, dielectric loss factor, tracking resistance and the electrical corrosive effect of polyamides are considerably impaired by the addition of ionic stabilisers, particularly after conditioning. In addition, ionic stabilisers frequently effloresce because of their solubility in water and, in so doing, form faults, such as spots or local discolouration, on the surface of polyamide articles, which spoil their appearance.

Moreover, copper stabilisers are incompatible with certain coloured pigments, particularly sulphur-containing pigments, when incorporated into polyamides, and thereby undesirably affect colour.

Consequently, attempts have long been made to use non-ionic stabilisers based on aromatic amino and hydroxy compounds, and also phosphorus compounds which do not have any of the disadvantages referred to above. Unfortunately, stabilisers such as these often have an inadequate or only a moderate stabilising effect or, in many cases, give rise to serious discolouration on incorporation into the polyamide, particularly under the effect of light. This applies in particular to aromatic amines.

It has now been found that phosphorous acid esters corresponding to the general formula (I) below are highly effective, non-ionic and non-discolouring stabilizers for polyamides.

They have an excellent stabilising effect in polyamides which, in some cases, is considerably superior to that of hitherto proposed and commercially available stabilisers. This was in no way to be expected because substances similar in structure to the phosphorous acid esters according to the present invention have little or no effect as stabilisers.

Accordingly, the present invention provides novel phosphorous acid esters corresponding to the general formula (I)

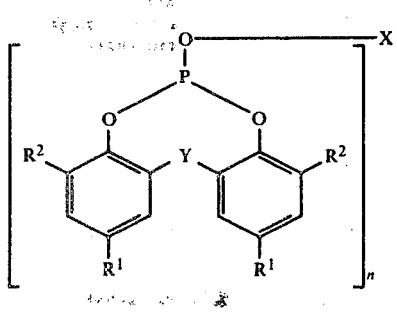

wherein
$R^2$ is a benzyl, α-methylbenzyl, α,α-dimethylbenzyl, cyclopentyl or cyclohexyl radical;
$R^1$ is a $C_1$-$C_9$ alkyl, a $C_5$-$C_6$ cycloalkyl, a $C_7$-$C_9$ aralkyl or a $C_6$-$C_{10}$ aryl radical;

Y is a sulphur atom or a group HC-$R^3$, in which $R^3$ is a hydrogen atom a $C_1$-$C_6$ alkyl, a cyclohexyl or cyclohexenyl radical;
X is a hydrogen atom, an optionally substituted single-bond to four-bond straight-chain or branched-chain $C_1$-$C_{18}$ aliphatic radical, A $C_7$-$C_{18}$ aralkyl radical or a $C_6$-$C_{18}$ aromatic radical, each of which radicals may optionally contain olefinic double bonds and/or hetero atoms, preferably N, O and/or S atoms, and
n is an integer from 1 to 4, preferably from 1 to 2, provided that when X is a hydrogen atom, the n is 1;
and the use of these compounds for stabilising polyamides.

Preferred substituents for the radicals defined for X are OH, $C_1$-$C_4$ alkoxy, amino, $C_1$-$C_8$ alkylamino, $C_1$-$C_8$ dialkylamino, SH, $C_1$-$C_4$ alkyl mercapto, $C_1$-$C_{12}$ alkyl, $C_7$-$C_{12}$ aralkyl, $C_6$-$C_{10}$ aroxy and $C_6$-$C_{10}$ aryl groups.

$R^1$ is advantageously, for example, $CH_3$, $C_2H_5$, $HC(CH_3)_2$, $C(CH_3)_3$, $C(CH_3)_2C_2H_2$, isononyl, isooctyl, benzyl, styryl, α-methyl styryl, cyclohexyl, cyclopentyl, preferably $CH_3$, $HC(CH_3)_2$, $C(CH_3)_3$, cyclohexyl, benzyl, α-methyl styryl, isononyl, more preferably $CH_3$, $C_2H_5$, $HC(CH_3)_3$, cyclohexyl, benzyl, styryl and, more preferably $CH_3$, $C_2H_5$.

X is preferably a hydrogen atom, a radical corresponding to formula (II)

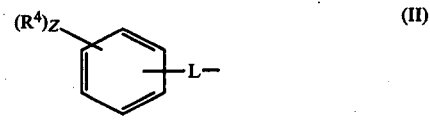

in which
—L— is a single bond or an alkyleneoxy group;
$R^4$ is a hydrogen atom, —L—, an aryl group, a condensed ring, a $C_1$-$C_9$ alkyl, $C_7$-$C_{12}$ alkaryl, $C_1$-$C_4$ alkyl mercapto, $C_1$-$C_4$ alkoxy, or a β-hydroxy alkoxy radical, an OH-group, an amino-group, or a SH-group or a

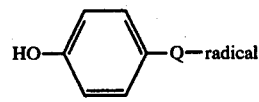

in which Q is a single bond, an O or S atom or a O—(CH$_2$)$_2$—O or $C_1$-$C_4$ alkylidene group; and
Z=1 or 2;
or a radical corresponding to formula (III)

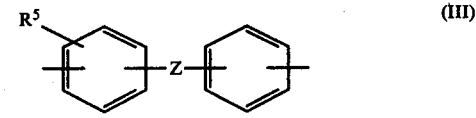

in which
$R^5$ is an OH-group or a hydrogen atom and
Z is a single bond, a $C_1$-$C_4$ alkylidene radical, an O or S atom or a O—(CH$_2$)$_2$—O group;
or a monofunctional or difunctional $C_1$-$C_{18}$ alkyl radical which is substituted by a phenyl, OH or phenoxy group and which may optionally be attached through ether bridges or S-bridges, a $C_1$-$C_9$ alkyl, a cyclohexyl or a tetralyl radical;
or a radical corresponding to formula (IV)

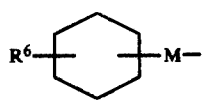

(IV) 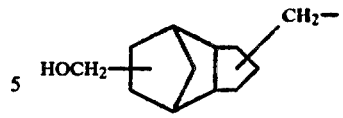

in which
—M— is an alkylene or alkylene cycloalkyl radical; and
$R^6$ is —M—, a hydroxyalkyl, a hydroxyalkoxy, an alkylene a hydrogen atom or a OH radical or a bond.
In addition, X may represent

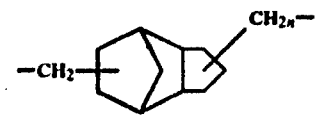

or the oxyalkylation products of glycerol, trimethylol propane or pentaerythritol containing from 3 to 8 oxyethyl or oxypropyl radicals.

The following compounds (corresponding to general formula I) are preferred:

| | | | $R^1 = CH_3$, | $R^2$ = cyclohexyl, | n = 1 |
|---|---|---|---|---|---|
| (1) | Y = $CH_2$, | X = phenyl, | " | benzyl | " |
| (2) | " | " | " | α-methylbenzyl | " |
| (3) | " | " | " | cyclohexyl | " |
| (4) | Y = S | " | " | benzyl | " |
| (5) | " | " | " | α-methylbenzyl | " |
| (6) | " | " | " | | " |
| (7) | Y = $CH_2$, | X = o-, m-, or p-cresyl | " | $R^2$ = α-methylbenzyl | " |
| (8) | " | " | " | benzyl | " |
| (9) | " | " | " | cyclohexyl | " |
| (10) | " | X = isononyl-phenyl | " | cyclohexyl | " |
| (11) | " | " | " | benzyl | " |
| (12) | " | " | " | α-methylbenzyl | " |
| (13) | " | X = β-naphthyl | " | cyclohexyl | " |
| (14) | " | " | " | benzyl | " |
| (15) | " | " | " | α-methylbenzyl | " |
| (16) | " | X = H | " | cyclohexyl | " |
| (17) | " | " | " | benzyl | " |
| (18) | " | " | " | α-methylbenzyl | " |
| (19) | " | X = benzylphenyl | " | cyclohexyl | " |
| (20) | " | " | " | benzyl | " |
| (21) | " | " | " | α-methylbenzyl | " |
| (22) | " | X = phenylphenyl | " | cyclohexyl | " |
| (23) | " | " | " | benzyl | " |
| (24) | " | " | " | α-methylbenzyl | " |
| (25) | " | X = HO—⟨⟩—⟨⟩— | " | cyclohexyl | " |
| (26) | " | " | " | benzyl | " |
| (27) | " | " | " | α-methylbenzyl | " |
| (28) | " | X = —⟨⟩—⟨⟩— | " | cyclohexyl | 2 |
| (29) | " | " | " | benzyl | " |
| (30) | " | " | " | α-methylbenzyl | " |
| (31) | " | X = stearyl | " | cyclohexyl | 1 |
| (32) | " | " | " | benzyl | " |
| (33) | " | " | " | α-methylbenzyl | " |
| (34) | " | X = m or p-hydroxyphenyl | " | $R^2$ = cyclohexyl | " |
| (35) | " | " | " | benzyl | " |
| (36) | " | " | " | α-methylbenzyl | " |
| (37) | " | X = HO—⟨⟩—S—⟨⟩ | " | cyclohexyl | " |
| (38) | " | X = —⟨⟩—S—⟨⟩— | " | " | 2 |
| (39) | " | X = —$CH_2$—$CH_2$O—⟨⟩ | " | " | 1 |
| (40) | " | X = HO—$CH_2$—⟨⟩—$CH_2$ | " | " | " |
| (41) | " | X = $CH_2$—⟨⟩—$CH_2$— | " | $R^2$ = cyclohexyl | 2 |
| (42) | " | X = $HO(CH_2)_6$— | " | " | 1 |
| (43) | " | X = —$(CH_2)_6$— | " | " | 2 |
| (44) | " | X = $HOCH_2CH_2SCH_2CH_2$— | " | " | 1 |
| (45) | " | X = $CH_2CH_2SCH_2CH_2$— | " | " | 2 |
| (46) | " | X = $HOCH_2CH_2(OCH_2CH_2)_6$ | " | " | 1 |

-continued

| | | | | | |
|---|---|---|---|---|---|
| (47) | " | X = —OCH₂CH₂<br>CH₂CH₂(OCH₂CH₂)₆<br>—OCH₂CH₂— | " | " | 2 |
| (48) | " | X = —SCH₃ | " | " | 1 |
| (49) | " | X = —⟨phenyl⟩—N(CH₃)₂ | " | " | 1 |
| (50) | " | X = —⟨phenyl⟩—OCH₃ | " | " | 1 |
| (51) | " | X = dodecyl | " | " | 1 |
| (52) | Y = CH—CH,<br>with CH₃ groups | X = H | " | " | 1 |
| (53) | Y = CH₂, | X = HOCH₂CH₂O—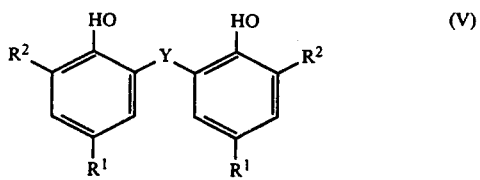—OCH₂CH₂—" | " | " | 2 |
| (54) | Y = S, | X = H | " | " | 1 |
| (55) | " | " | " | " | " |
| (56) | " | " | " | α-methylbenzyl | " |
| (57) | Y = CH—CH₃ | " | " | " | " |
| (58) | Y = S | " | H | R² = benzyl | " |

Starting products suitable for the production of the inventive phosphorous acid esters of formula (I) are:
(1) bisphenols corresponding to formula (V)

(V)

wherein R¹, R² and Y are as defined herein above.

More particularly, R¹ preferably represents CH₃, C₂H₅, HC(CH₃)₂, C(CH₃)₃, C(CH₃)₂C₂H₅, isononyl, isooctyl, benzyl, styryl, α-methyl styryl, cyclohexyl, cyclopentyl, whilst Y preferably represents S, CH₂, CH-CH₃, CH-CH(CH₃)₂, CHCH₂CH₂CH₃ or

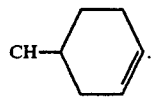

The following compounds may be used, for example, for producing the stabilisers according to the present invention:

(1)

bis-(2-hydroxy-3-cyclohexyl-5-methyl-phenyl)-methane
bis-(2-hydroxy-3-cyclohexy-5-methyl-phenyl)-sulphide
bis-(2-hydroxy-3-benzyl-5-methyl-phenyl)-methane
bis-(2-hydroxy-3-benzyl-5-methyl-phenyl)-sulphide
bis-(2-hydroxy-3-styryl-5-methyl-phenyl)-methane
bis-(2-hydroxy-3-styryl-5-methyl-phenyl)-sulphide
bis-(2-hydroxy-3-cyclohexyl-5-methyl-phenyl)-1,1-isobutane
bis-(2-hydroxy-3-styryl-5-methyl-phenyl)-1,1-isobutane
bis-(2-hydroxy-3-cyclohexyl-5-methyl-phenyl)-1,1-ethane (2)

phosphorous acid derivatives corresponding to formula (IV)

PW₃ (VI)

wherein

W is a halogen atom or a OR⁷ group in which

R⁷ is a C₁–C₁₅ alkyl, C₅–C₆ cycloalkyl, C₇–C₁₅ aralkyl or C₆–C₁₀ aryl group; provided that R⁷=H may only occur once in the formula VI.

W preferably represents Cl, Br, whilst R⁷ is preferably H, CH₃, C₂H₅, C₄H₉, phenyl, cresyl, or isononyl phenyl.

Suitable phosphorous acid derivatives of formula (VI) are, for example, phosphorus trichloride, trimethyl phosphite, triethyl phosphite, triphenyl phosphite, tricresyl phosphite, tris-isononyl-phenyl phosphite, dimethylphosphite, diethyl phosphite, diphenyl phosphite and dicresyl phosphite.

(3)

Monohydroxy and polyhydroxy compounds corresponding to the general formula (VII)

X(OH)ₙ (VII)

wherein n and X are as defined herein above.

Suitable monohydroxy and polyhydroxy compounds are, for example, o-, m-, or p-cresol, 2,4-dimethyl phenol, 3,5-dimethyl phenol, isononyl phenol, benzyl phenol, styryl phenol, p-methyl mercapto phenol, o-, m-, or p-methoxy phenol m-(N,N-dimethylamino)-phenol, o or p-phenylphenol, p-hydroxy phenol, 4,4'-dihydroxydiphenylmethane, 4,4'-dihydroxy-2,2-diphenyl propane, 4,4'-dihydroxydiphenyl, 4,4'-dihydroxydiphenyl ether, 4,4'-dihydroxydiphenyl sulphide, water, methanol, ethanol, octanol, dodecanol, stearyl alcohol, phenoxy ethanol, benzyl alcohol, cyclohexane dimethanol, perhydrogenated 4,4'-dihydroxy-2,2-dicyclohexyl propane, 1,6-hexane diol diglycol, triglycol, tetraglycol, octaethylene glycol, thiodiglycol, bis-ethoxyl-bisphenol A, bis-ethoxyl hydroquinone, ethoxylated glycerol and ethoxylated pentaerythritol containing from 3 to 8 oxyethyl radicals.

The compounds according to the invention are produced by processes analogous to those known per se, the following variants being possible:

For example the bisphenols used as starting products may be reacted with triaryl or trialkyl phosphites, preferably triphenyl, trimethyl or triethyl phosphite, at temperatures in the range of from 50° to 300° C. and preferably at temperatures in the range of from 80° to 250° C., and the hydroxy compounds formed, such as phenol, methanol or ethanol, are distilled off, which in the case of highboiling hydroxy compounds is best performed under reduced pressure. The reaction may be accelerated by using typical transesterification catalysts, for example alkali metals and their derivatives, such as oxides, hydroxides, carbonates and their salts with carboxylic acid, compounds of tetravalent titanium, such as titanium tetrabutylate and titanium tetraphenolate, and organotin compounds, such as dibutyl tin dilaurate, dibutyl tin oxide and dibutyl tin diphenolate.

The molar ratio between these reactants is not particularly critical. In general, the reactnts are used in a ratio of 1:1, but the phosphite reactant may readily be used in an excess of up to 10-fold and then the excess may be recovered upon completion of the reaction.

After two equivalents of the hydroxy compound originally bound to the phosphite have been separated off from the reaction mixture, the third remains in the newly formed phosphorous acid ester of bisphenol, i.e. where triphenyl phosphite is used for example, as the startingproduct, X in formula (I) is a phenyl radical.

In cases where X is intended to be different from the radicals which are introduced by means of the starting phosphite, it is replaced in a subsequent transesterification step. If, for example, X is to be $\beta$-naphthyl, the bisphenol phosphite initially formed (X=phenyl) is reacted with the corresponding hydroxy compound, i.e. $\beta$-naphthol, and phenol is distilled off. This second reaction step is carried out under the conditons described above for the first reaction step. However, the molar ratios should be selected in accordance with the desired products. In the example just described therefore, $\beta$-naphthol is reacted with the cyclic phosphorous acid ester in a molar ratio of 1:1. Depending on the desired product, a dihydroxy compound, for example, 1,6-hexane diol, may be reacted with the bisphenol phosphite in a molar ratio of 1:1 or $\frac{1}{2}$:1 and a trihydroxy compound in a ratio of 1:1, $\frac{1}{2}$:1 and $\frac{2}{3}$:1.

However, the hydroxy compund by means of which the new radical X is to be introduced, for example $\beta$-naphthol, may also be initially reacted with the trialkyl or triaryl phosphite and then with the bisphenol. However, it may also be simultaneously reacted with the bisphenol.

When X=H, it is best to use dialkyl or diaryl phosphites as starting products and then to remove two equivalents of hydroxy compound from the reaction mixture by distillation. The dialkyl or diaryl phosphites may readily be formed in situ from the trialkyl or triaryl phosphites by adding the calculated quantity of water.

Basically, the radical X may also be split off from the preformed bisphenol phosphite by using water, although this is generally more complicated.

The inventive stabilizers may also be obtained by reacting the bisphenols and the hydroxy compounds carrying the desired group X with phosphorus trihalides, particularly phosphorus trichloride, with elimination of hydrogen halides. However, this method does not afford any significant advantages over the methods described above.

Synthetic polyamides of the type obtained by the polycondensation of diamines with dicarboxylic acids, by the polymerisation of lactams or by the polycondensation of aminocarboxylic acids, may be stabilised with the stabilisers according to the present invention. The stabilizers according to the present invention are preferably used for stabilising aliphatic polyamides, particularly those of adipic acid and hexamethylene diamine or of caprolactam, or mixed polyamides in which these components represent the main constituents.

The stabilization with the inventive compounds has the following advantages: The polyamides are stabilized against degradation under heat. Colouration of the stabilized polyamides even if containing sulfidic pigments cannot be observed. The stabilizers do not emigrate to the surface of the polyamide. Important electrical properties of the polyamide are outstanding improved.

The stabilizers according to the invention are used in quantities of from 0.02 to 5% by weight, preferaby in quantities of from 0.05 to 2% by weight and, with particular preference, in quantities of from 0.1 to 1.5% by weight, based on the weight of the polyamide to be stabilized. They may be incorporated before or during the production of the polyamide or after the polymerization, the stabilizers being used either as such or in the form of a solution in an inert solvent or in one of the polyamide-forming starting materials or even in the form of a concentrate in a suitable polymer, preferably in a polyamide. The stabilizers are preferably incorporated into the polyamide melt using known mixers, such as extruders, kneaders, static mixers and stirrers. Various additives of the type and amount normally used, such as lubricants and mould-release agents, nucleating agents, pigments, dyes, reinforcing or non-reinforcing fillers such as mineral fibres, glass and asbestos fibres, microbeads of glass, tacum, silicon dioxide or mica, antistatic agents, plasticizers and UV-stabilizers, may also be added to the polyamides.

The polyamides stabilized by using the compounds according to the present invention are eminently suitable for the production of technical rayon for fishing nets, drive belts, conveyor belts, tyre cord or mouldings which are subjected to thermal stressing in the presence of air or oxygen.

EXAMPLE 1

Phosphorous acid ester of phenol and bis-(2-hydroxy-3-cyclohexyl-5-methyl-phenyl)-methane:

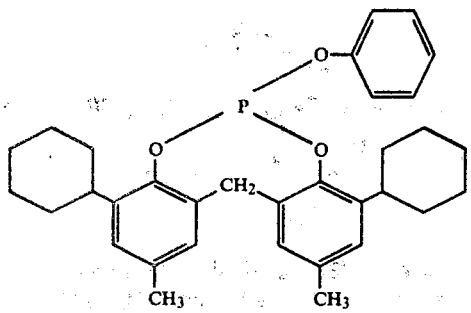

A mixture of 392 g (1 mole) of bis-(2-hydroxy-3-cyclohexyl-5-methyl-phenyl)-methane, 310 g (1 mole) of triphenyl phosphite, 10 g of diphenyl phosphite and 0.4 g of lithium hydroxide is heated, with stirring, at from 160° to 225° C. over a period of 10 hours at 12 to 13 Torr, 188 g (2 moles) of phenol being distilled off. 512 g of a pale yellowish melt which hardens like glass is obtained as residue. The product is obtained in crystalline form after dissolution in hot ligroin.

M.p. 164° to 166° C.

Molecular weight: observed 508, calculated 514.65.

Analysis for $C_{33}H_{39}PO_3$:

| % C | calculated | 77.02 | observed | 6.67 |
| % H | calculated | 7.64 | observed | 8.00 |
| % P | calculated | 6.02 | observed | 6.24 |
| % O | calculated | 9.33 | observed | 9.10 |

EXAMPLE 2

Phosphorous acid ester of phenol and bis-(2-hydroxy-3-styryl-5-methyl-phenyl)-methane:

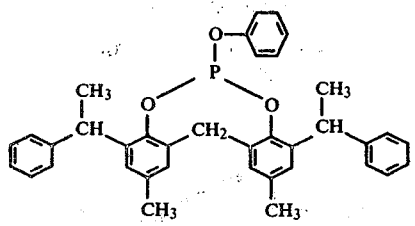

A mixture of 218 g (0.5 mole) of bis-(2-hydroxy-3-styryl-5-methyl-phenyl)-methane and 155 g (0.5 mole) of triphenyl phosphite is heated, with stirring, at from 170° to 250° C. over a period of 8 hours at 16 to 18 Torr, 94 g (1 mole) of phenol distilling off. 276 g of a pale yellow melt which hardens to form a brittle mass is obtained.

| $C_{37}H_{35}PO_3$ (558.66) | % C | calculated | 79.55 | observed | 79.09 |
| | % H | calculated | 6.32 | observed | 6.57 |
| | % P | calculated | 5.54 | observed | 5.12 |

EXAMPLE 3

Phosphorous acid ester of phenol and bis-(2-hydroxy-3-benzyl-5-methyl-phenyl)-methane:

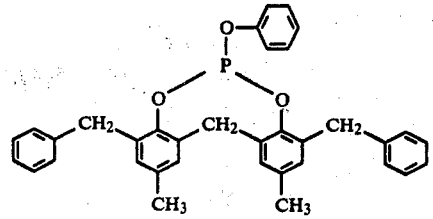

A mixture of 204 g (0.5 mole) of bis-(2-hydroxy-3-benzyl-5-methyl-phenyl)-methane and 155 g of triphenyl phosphite is heated at from 160° to 230° C. over a period of 6 hours at 14 Torr, a total of 92 g of phenol distilling over. 263 g of a yellowish resin are obtained.

EXAMPLE 4

Phosphorous acid ester of bis-(2-hydroxy-3-cyclohexyl-5-methyl-phenyl)-methane and 1 mole of octa-ethylene glycol:

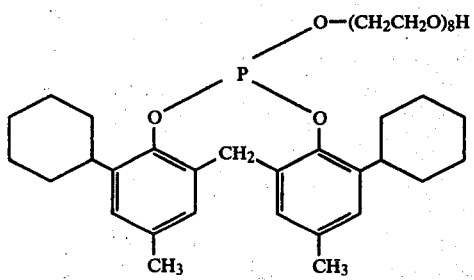

A mixture of 514 g (1 mole) of the phosphorous acid ester prepared in accordance with Example 1 and 370 g (1 mole) of octa-ethylene glycol is heated at from 200° to 250° C. over a period of 2.5 hours at 20 Torr, 90 g of phenol distilling off. The reaction product is a yellowish resin (790 g).

EXAMPLE 5

Phosphorous acid ester of bis-(2-hydroxy-3-cyclohexyl-5-methyl-phenyl)-methane and 0.5 mole of octaethylene glycol:

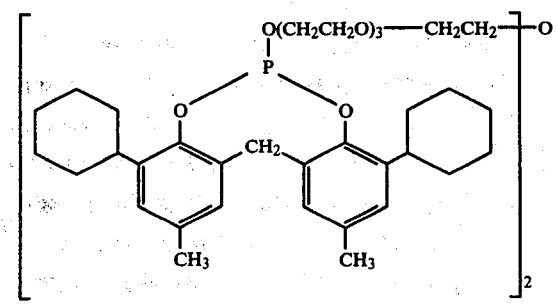

A mixture of 514 g (1 mole) of the phosphorous acid ester prepared in accordance with Example 1 and 185 g (0.5 mole) of octa-ethylene glycol is heated at from 230° to 250° C. over a period of 4 hours at 30 Torr, 89 g of phenol distilling off. A yellow resin is obtained as the reaction product (610 g).

EXAMPLE 6

Phosphorous acid ester of bis-(2-hydroxy-3-cyclohexyl-5-methyl-phenyl)-methane and stearyl alcohol:

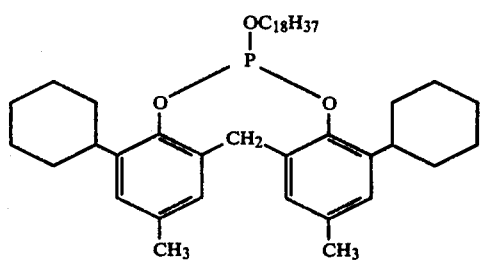

A mixture of 103 g (0.2 mole) of the phosphorous acid ester prepared in accordance with Example 1 and 53 g (0.2 mole) of stearyl alcohol is heated at from 155° to 245° C. over a period of 12 hours at 16 Torr, 16 g of phenol distilling over. The residue is a yellowish opaque resin.

EXAMPLE 7

Phosphorous acid ester of bis-(2-hydroxy-3-cyclohexyl-5-methyl-phenyl)-methane:

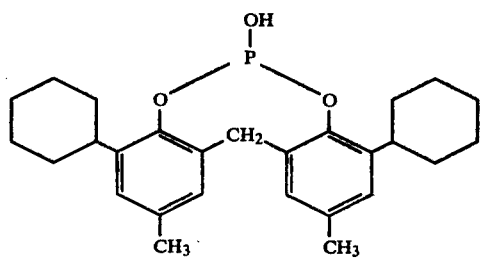

A mixture of 392 g (1 mole) of bis-(2-hydroxy-3-cyclohexyl-5-methyl-phenyl)-methane, 310 g (1 mole) of triphenyl phosphite and 18 g (1 mole) of water is heated under a nitrogen atmosphere at normal pressure to 180° C. After cooling to 100° C., the mixture is heated at from 100° to 200° C. over a period of 2.5 hours at 25 Torr, 270 g of phenol distilling over. An almost colourless, slowly crystallising product is left as residue (450 g).

M.p.: 180° to 181° C. (from xylene), MW 403 (calculated 438).

EXAMPLE 8

Phosphorous acid ester of bis-(2-hydroxy-3-benzyl-5-methylphenyl)-sulphide:

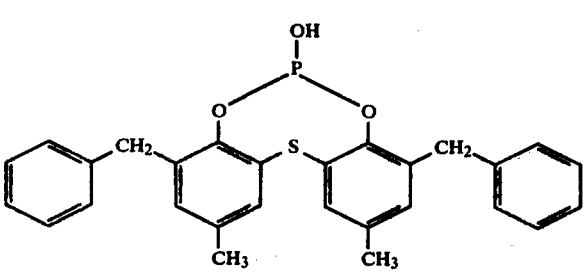

A mixture of 213 g of bis-(2-hydroxy-3-benzyl-5-methyl-phenyl)sulphide (0.5 mole), 155 g (0.5 mole) of triphenyl phosphite and 9 g (0.5 mole) of water is first heated to 180° C. under a nitrogen atmosphere at normal pressure and, after cooling to 100° C., is then heated at from 100° to 200° C. over a period of a few hours at 25 Torr, 135 g of phenol distilling over. The reaction product (250 g) is a yellowish resin.

EXAMPLE 9

Phosphorous acid ester of bis-(2-hydroxy-3-benzyl-5-methyl-phenyl)-methane:

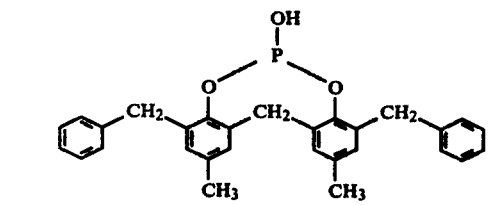

A mixture of 77.5 g (0.25 mole) of triphenyl phosphite, 4.5 g (0.25 mole) of water and 102 g (0.25 mole) of bis-(2-hydroxy-3-benzyl-5-methyl-phenyl)-methane is reacted in the same manner as in Example 7, 69 g of phenol distilling over. 118 g of the title compound is obtained in the form of a yellowish resin.

EXAMPLE 10

Phosphorous acid ester of bis-(2-hydroxy-3-cyclohexyl-5-methyl-phenyl)sulphide

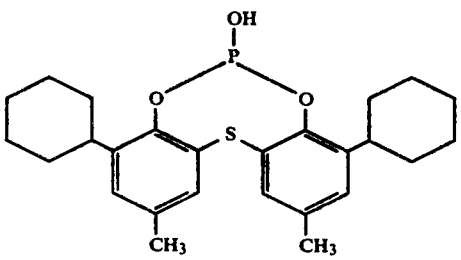

A mixture of 41 g (0.1 mole) of bis-(2-hydroxy-3-cyclohexyl-5-methyl-phenyl)-sulphide, 31 g (0.1 mole) of triphenyl phosphite and 1.8 g (0.1 mole) of water is heated with stirring under a nitrogen atmosphere to 180° C., cooled to 100° C., and then heated at from 100° to 250° C. over a period of 5 hours at 12 to 13 Torr, 27 g of phenol distilling over. 45 g of a solid pale yellow resin are left as reaction product. Crystals melting at 122° C. are obtained from ligroin.

| C$_{26}$H$_{33}$PO$_3$S (456.59) | % C | calculated | 68.35 | observed | 68.13 |
|---|---|---|---|---|---|
| | % H | calculated | 7.29 | observed | 7.52 |
| | % P | calculated | 6.78 | observed | 6.43 |
| | % S | calculated | 7.02 | observed | 7.28. |

EXAMPLE 11

Phosphorous acid ester of bis-(2-hydroxy-3-cyclohexyl-5-methl-phenyl)-methane and β-naphthol

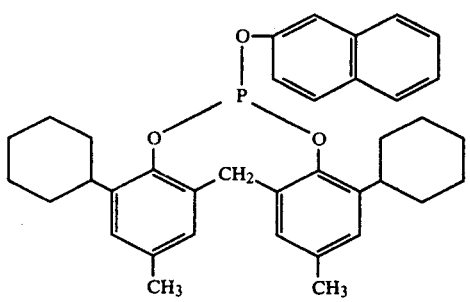

51 g (0.1 mole) of the compound prepared by the method of Example 1 and 14 g (0.1 mole) of β-naphthol are reacted at 115 to 118 mb and at 220° to 280° C. (sump temperature) in the presence of 0.05 g of lithium hydroxide, 8.5 g of phenol distilling off. A clouded, yellowish hard resin (56.5 g) is obtained, giving crystals from petroleum ether melting at 128° C.

EXAMPLE 12

Phosphorous acid ester of bis-(2-hydroxy-3-cyclohexyl-5-methyl-phenyl)-methane and 4,4'-dihydroxy-2,2-diphenyl propane

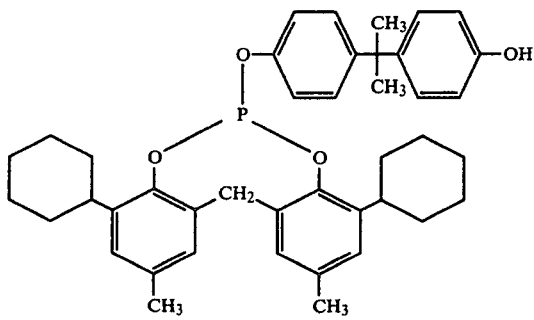

103 g (0.2 mole) of the compound produced by the method of Example 1 and 46 g (0.2 mole) of 4,4'-dihydroxy-2,2-diphenyl propane are reacted at 1.5 to 2.0 mb and at 140° to 270° C. (sump temperature), 18 g of phenol distilling off. 128 g of a clouded yellowish hard resin are obtained. Crystals melting at 129° to 131° C. are obtained from petroleum ether/xylene.

EXAMPLE 13

Phosphorous acid ester of bis-(2-hydroxy-3-cyclohexyl-5-methyl-phenyl)-methane and 4-hydroxy-diphenyl

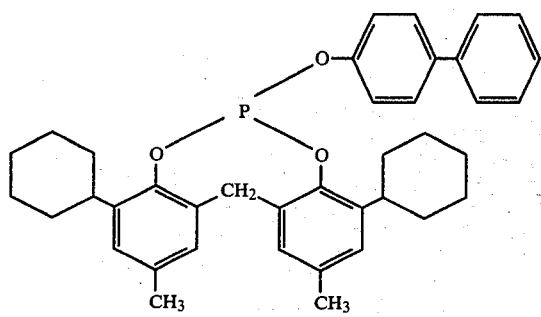

128 g (0.25 mole) of the phosphorous acid ester produced by the method of Example 1 and 42 g (0.25 mole) of 4-hydroxydiphenyl are reacted over a period of 2 to 3 hours at 17 Torr and at 115° to 220° C. (sump temperature) in the presence of 0.1 g of lithium hydroxide, 22 g of phenol distilling off. A pale yellowish hard resin (148 g) is obtained, giving crystals from ligroin melting at 165° to 170° C.

EXAMPLE 14

Phosphorous acid ester of bis-(2-hydroxy-3-cyclohexyl-5-methyl-phenyl)-methane and 4,4'-dihydroxydiphenyl sulfide

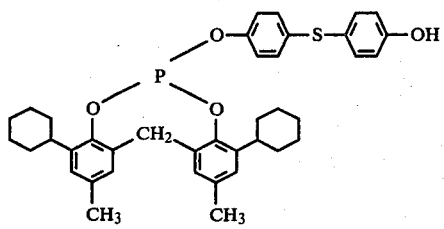

128 g (0.25 mole) of the compound prepared by the method of Example 1 and 46 g (0.25 mole) of 4,4-dihydroxydiphenyl sulphide are reacted over a period of 1 to 2 hours at 18 Torr and at 130° to 220° C. (sump temperature), 22 g of phenol distilling off. The light brown resin (153 g) left behind is obtained in crystalline form from ligrion/xylene, m.p. 128° to 133° C.

EXAMPLE 15

Phosphorous acid ester of N,N-dimethyl-m-aminophenol and bis-(2-hydroxy-3-cyclohexyl-5-methyl-phenyl)-methane

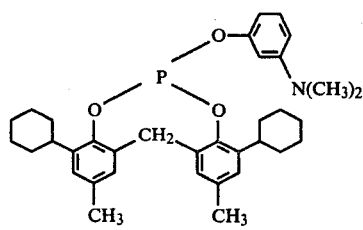

A mixture of 51.5 g (0.1 mole) of the compound prepared by the method of Example 1 and 13.8 g (0.1 mole) of N,N-dimethyl-m-aminophenol is heated at from 150° to 195° C. over a period of 3 hours at 17 Torr, 9.1 g of phenol distilling off with stirring through a small column. 56 g of a brittle brown resin is obtained.

EXAMPLE 16

Phosphorous acid ester of thiodiglycol and bis-(2-hydroxy-3-styryl-5-methylphenyl)-methane

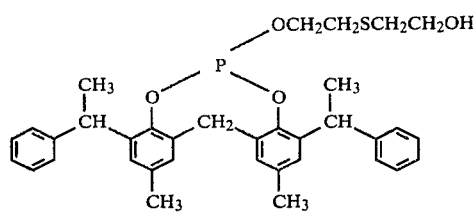

A mixture of 55.9 g (0.1 mole) of the compound prepared by the method of Example 2 and 12.2 g (0.1 mole) of thiodiglycol is reacted following the procedure of Example 15. 57 g of a yellow brittle resin is obtained.

EXAMPLE 17

Phosphorous acid ester of triethanolamine and bis-(2-hydroxy-3-styryl-5-methyl-phenyl)-methane

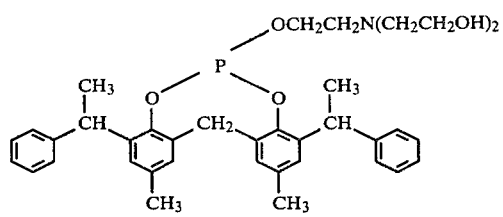

A mixture of 55.9 g (0.1 mole) of the compound prepared by the method of Example 2 and 14.9 g (0.1 mole) of triethanolamine is reacted following the procedure of Example 15. In addition to 9.0 g of phenol distillate, 70 g of a soft yellow resin are obtained.

TESTING THE STABILISING EFFECT IN UNREINFORCED POLYAMIDE-6

To test the stabilising effect, the substance to be tested was homogeneously worked into polyamide-6 ($\eta_{rel}=4.0$) in a concentration of 0.5% by weight by passage through an extruder. The material thus stabilised was injection-moulded to form standard small test bars and these were then subjected to thermal ageing in the presence of air at 150° C.±0.5° C. After 1, 2, 4, 8 etc. days, 8 standard small test bars were removed and, after cooling for 2 hours in a desiccator, were tested for impact strength in accordance with DIN No. 53 453. The test specimens pass the test if at least half remain unbroken or if the average impact strength of the broken test specimens is above 30 kJ/m². The stabilising effect is evaluated in stages in accordance with the following Table;

| Thermal ageing time up to failure of the impact test | 1 | 2 | 4 | 8 | 16 etc. days |
|---|---|---|---|---|---|
| Activity stage of the stabiliser | 0 | 1 | 2 | 3 | 4 etc. |

The testing of stabilisers according to the invention produced the following results:

| Stabiliser (0.5% by weight) | | Activity Stage |
|---|---|---|
| of Example | 1 | 4 |
| | 2 | 3 |
| | 3 | 2 to 3 |
| | 4 | 3 |
| | 5 | 3 |
| | 6 | 3 |
| of Example | 7 | 4 |
| | 8 | 2 to 3 |
| | 10 | 2 to 3 |
| | 12 | 4 to 5 |

None of the stabilisers causes any discolouration on incorporation into the polyamide.

Some standard commercially available stabilisers and phosphorous acid esters which are not within the scope of the present invention were tested for comparison. The following results were obtained:

| Stabiliser (0.5% by weight) | Activity Stage |
|---|---|
| I | 0 |
| II | 1 to 2 |
| III | 1 to 2 |
| IV | 1 to 2 |
| V | 1 to 2 |
| VI | 0 |
| VII | 2 |

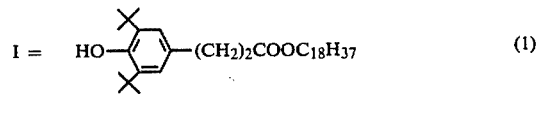

(Irganox 1076) ®     (1)

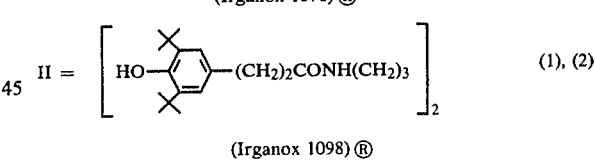

(Irganox 1098) ®     (1), (2)

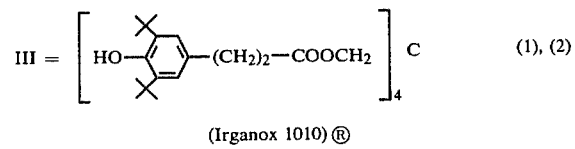

(Irganox 1010) ®     (1), (2)

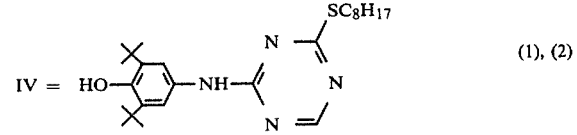

(1), (2)

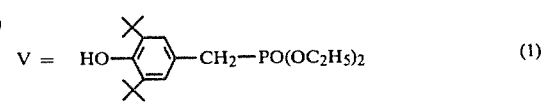

(1)

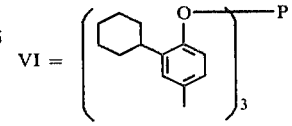

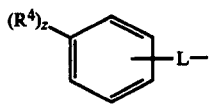

wherein
—L— is a single bond or an alkyleneoxy moiety,
$R^4$ is a single bond, an alkyleneoxy moiety, a condensed ring, an aryl, alkyl, alkaryl, alkyl mercapto, alkoxy, β-hydroxy alkoxy, OH—, amino-, SH— or a moiety of the formula

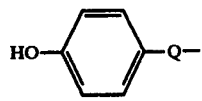

wherein Q is a single bond, an O or S atom, an O—(CH$_2$)$_2$—O or $C_1$-$C_4$-alkylidene, and
Z=1 or 2; or
(b) a moiety of the formula

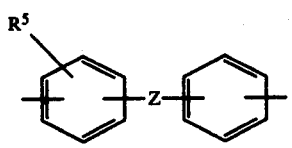

wherein
$R^5$ is hydroxy or hydrogen and
Z is a single bond, an alkylidene, O—(CH$_2$)$_2$—O, an O or S atom; or
(c) a monofunctional or difunctional alkyl unsubstituted or substituted by phenyl, OH or phonoxy and which may optionally be attached through ether bridges or S-bridges, an alkyl, cyclohexyl or a tetralyl radical or;
(d) a moiety of the formula

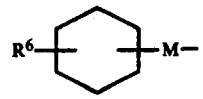

wherein
M is an alkylene or alkylene cycloalkyl; and
$R^6$ is a single bond, a hydroxyalkyl, a ω-hydroxyalkoxy, or an alkylene, an alkylene cycloalkyl, a hydrogen atom, or a hydroxy; or
(e) a moiety of the formula

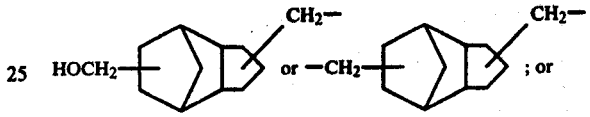

(f) an oxyalkylation product of glycerol, trimethylol propane or pentaerythritol containing from 3 to 8 oxyethyl or oxypropyl moieties; and
n is an integer of from 1 to 4, provided that when X is a hydrogen atom the n is equal to 1.

2. Phosphorous acid esters as claimed in claim 1, wherein $R^2$, $R^1$, Y, X and n has the following meaning:

| Y | X | $R^1$ | $R^2$ | n |
|---|---|---|---|---|
| Y = CH$_2$, | X = phenyl, | $R^1$ = CH$_3$, | $R^2$ = cyclohexyl, | n = 1 |
| " | " | " | benzyl | " |
| " | " | " | α-methylbenzyl | " |
| Y = S | " | " | cyclohexyl | " |
| " | " | " | benzyl | " |
| " | " | " | α-methylbenzyl | " |
| Y = CH$_2$, | X = o,m,p-cresyl, | $R^1$ = CH$_3$, | $R^2$ = α-methylbenzyl | n = 1 |
| " | " | " | benzyl | " |
| " | " | " | cyclohexyl | " |
| Y = CH$_2$, | X = isononyl-phenyl | " | cyclohexyl | " |
| " | " | " | benzyl | " |
| " | " | " | α-methylbenzyl | " |
| " | X = β-naphthyl | " | cyclohexyl | " |
| " | " | " | benzyl | " |
| " | " | " | α-methylbenzyl | " |
| " | X = H | " | cyclohexyl | " |
| " | " | " | benzyl | " |
| " | " | " | α-methylbenzyl | " |
| " | X = benzylphenyl | " | cyclohexyl | " |
| " | " | " | benzyl | " |
| " | " | " | α-methylbenzyl | " |
| Y = CH$_2$, | X = phenylphenyl | " | cyclohexyl | " |
| " | " | " | benzyl | " |
| " | " | " | α-methylbenzyl | " |
| " | " | " | cyclohexyl | " |
| " | X = HO—⟨⟩—⟨⟩— | | | |
| " | " | " | benzyl | |
| " | " | " | α-methylbenzyl | " |
| " | " | " | cyclohexyl | 2 |
| " | X = —⟨⟩—⟨⟩— | | | |
| " | " | " | benzyl | |
| " | " | " | α-methylbenzyl | " |
| " | X = stearyl | " | cyclohexyl | 1 |
| " | " | " | benzyl | " |
| " | " | " | α-methylbenzyl | " |

| Stabiliser (0.5% by weight) | Activity Stage |
|---|---|
| I | 0 |
| II | 1 to 2 |
| III | 1 to 2 |
| IV | 1 to 2 |
| V | 1 to 2 |
| VI | 0 |
| VII | 2 |

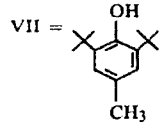

(1): Products of Ciba Geigy
(2): Specifically recommended for stabilising polyamides (see the following Ciba-Geigy publications: Publ. No. 770.512/d/Str./10 and 770.620/d/Str./10)
(3): A product of Metallgesellschaft AG.

TESTING THE STABILISING EFFECT IN GLASS-FIBRE-REINFORCED POLYAMIDE-6

The substance to be tested was worked into glass-fibre-reinforced polyamide-6 (30% of glass fibres) in a concentration of 0.5% by weight by passage through an extruder. The material thus stabilised was injection-moulded to form standard small test bars and these were then subjected to thermal ageing in the presence of air at 150° C.±0.5° C. For testing, 8 standard small test bars were removed and, after cooling for 2 hours in a desiccator, were tested for impact strength in accordance with DIN No. 53 453. The results (in kJ/m²) are set out in the following Table:

| Stabiliser | Thermal ageing time (days) | | | |
|---|---|---|---|---|
| | 0 | 1 | 4 | 8 |
| none (for comparison) | 46.0 | 27.1 | 25.3 | 24.2 |
| of Example 7 | 45.0 | 54.6 | 36.2 | 30.2 |
| of Example 1 | 52.7 | 58.8 | 38.9 | 33.7 |
| of Example 6 | 44.1 | 37.1 | 29.5 | 28.2 |
| II (for comparison) | 45.3 | 32.4 | 17.0 | 23.5 |

Electrical properties measured on stabilized glass-fibre-reinforced polyamides. The stabilizer is homogeneously distributed in the glass-fibre reinforced polyamide by means of an extruder. In the following table the electrical properties of such polyamides are set forth.

| polyamide | stabilizer | DIN 53 480 tracking resistance KB (stage) | DIN 53 482 surface resistance $R_{OC}$ (ohm) | | DIN 53 482 volume resistivity (ohm . cm) | | DIN 53 408 electrolyte corrosion (stage) |
|---|---|---|---|---|---|---|---|
| | | | dry 1.5% | H₂O | dry 1.5% | H₂O | |
| PA-6 + 30% by weight glassfibers | — | 475 | $2.10^{15}$ | $2.10^{13}$ | $6.10^{15}$ | $5.10^{12}$ | AN 1,6 |
| PA-6 + 30% by weight glassfibers | ionic stabilizer based on Cu | 325 | $2.10^{13}$ | $5.10^{12}$ | $3.10^{15}$ | $4.10^{11}$ | A/B 3 |
| PA-6 + 30% by weight glassfibers | of Example 7 0.5 % | 425 | $5.10^{13}$ | $5.10^{13}$ | $9.10^{15}$ | $1.10^{13}$ | AN 1,2 |
| PA-6 + 30% by weight glassfibers | of Example 1 0.5 % | 475 | $3.10^{13}$ | $5.10^{13}$ | $1.10^{16}$ | $1.10^{13}$ | AN 1,2 |
| PA-6.6 + 30% by weight glassfibers | — | 550 | $3.10^{13}$ | $3.10^{12}$ | $5.10^{15}$ | $2.10^{12}$ | AN 1,6 |
| PA-6.6 + 30% by weight glassfibers | of Example 7 0,5 % | 575 | $3.10^{13}$ | $1.10^{12}$ | $6.10^{15}$ | $1.10^{12}$ | AN 1,2 |

Comparison tests show that the stabilizers according to the invention are far superior to known non-ionic stabilizers in their stabilizing effect and to ionic stabilizers in the electrical properties of the polyamide containing them.

concentration of 0.5% by weight by passage through an extruder. The material thus stabilised was injection-moulded to form standard small test specimens and these were then subjected to thermal ageing in the presence of air at 120° C.±0.5° C. After 7, 14 and 21 days, 8 standard small test bars were removed and, after cooling for 2 hours in a desiccator, were tested for impact strength in accordance with DIN No. 53 453. The results obtained (in kJ/m²) are set out in the following Table:

| Stabiliser | Thermal ageing time | | | |
|---|---|---|---|---|
| | 0 | 7 | 14 | 21 days |
| none (for comparison) | 48.2 | 22.8 | 24.0 | 23.2 |
| of Example 7 | 50.5 | 35.5 | 34.7 | 30.4 |
| of Example 1 | 45.3 | 36.4 | 30.7 | 30.2 |
| II (for comparison) | 49.9 | 31.8 | 26.2 | 22.8 |
| VII (for comparison) | 48.9 | 29.9 | 22.5 | 24.1 |

TESTING THE STABILISING EFFECT IN GLASS-FIBRE-REINFORCED POLYAMIDE-6,6

The substance to be tested was homogeneously worked into glass-fibre-reinforced polyamide-6,6 (30% of glass fibres) in a concentration of 0.5% by weight by passage through an extruder. The material thus stabilised was injection-moulded to form standard small test bars and these were then subjected to thermal ageing in the presence of air at 150° C.±0.5° C. For testing, 8 standard small test bars were removed and, after cooling for 2 hours in a desiccator, were tested for impact strength in accordance with DIN No. 53 453. The results (in kJ/m²) are set out in the following Table:

We claim:
1. Phosphorous acid esters corresponding to the formula:

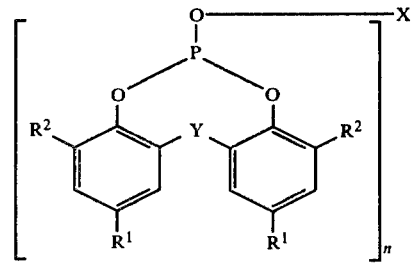

wherein
R² is a benzyl, α-methylbenzyl, α,α-dimethyl benzyl, cyclopentyl or cyclohexyl,
R¹ is an alkyl, a cycloalkyl, an aralkyl or an aryl,
Y is a sulphur atom or HC—R³ wherein R³ is a hydrogen atom, an alkyl, cyclohexyl or cyclohexenyl,
X is a hydrogen atom, or
(a) a moiety of the formula -continued

| | | | | |
|---|---|---|---|---|
| Y = CH$_2$, | X = m-p- or hydroxyphenyl | " | R$^2$ = cyclohexyl | " |
| " | " | " | benzyl | " |
| " | " | " | α-methylbenzyl | " |
| " | " | " | cyclohexyl | " |
| " | X = HO——S— | " | " | 2 |
| " | X = —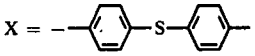—S—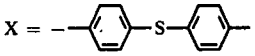— | " | " | 1 |
| " | X = —CH$_2$—CH$_2$O—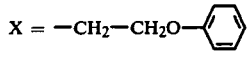 | " | " | " |
| " | X = HO—CH$_2$—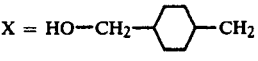—CH$_2$ | | | |
| Y = CH$_2$, | X = CH$_2$—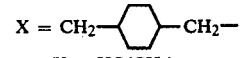—CH$_2$— | R$^1$ = CH$_3$, | R$^2$ = cyclohexyl | 2 |
| " | X = HO(CH$_2$)$_6$— | " | " | 1 |
| " | X = —(CH$_2$)$_6$— | " | " | 2 |
| " | X = HOCH$_2$CH$_2$SCH$_2$CH$_2$— | " | " | 1 |
| " | X = CH$_2$CH$_2$SCH$_2$CH$_2$— | " | " | 2 |
| " | X = HOCH$_2$CH$_2$(OCH$_2$CH$_2$)$_6$—OCH$_2$CH$_2$ | " | " | 1 |
| " | X = CH$_2$CH$_2$(OCH$_2$CH$_2$)$_6$—OCH$_2$CH$_2$— | " | " | 2 |
| " | X = ——SCH$_3$ | " | " | 1 |
| " | X = —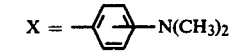—N(CH$_3$)$_2$ | " | " | 1 |
| " | X = ——OCH$_3$ | " | " | 1 |
| " | X = dodecyl | " | " | 1 |
| Y = CH—CH, with CH$_3$ / CH$_3$ | X = H | " | " | 1 |
| Y = CH$_2$, | X = HOCH$_2$CH$_2$O—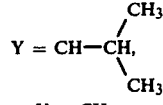—OCH$_2$CH$_2$— | " | " | 2 |
| Y = S, | X = H | " | " | 1 |
| " | " | " | " | " |
| " | " | " | α-methylbenzyl | " |
| Y = CH—CH$_3$ | " | " | " | " |
| Y = S | " | H | R$^2$ = benzyl | " |

* * * * *